US008381728B2

(12) United States Patent
Rao et al.

(10) Patent No.: US 8,381,728 B2
(45) Date of Patent: Feb. 26, 2013

(54) SELF-CLEANING AND STERILIZING ENDOTRACHEAL AND TRACHEOSTOMY TUBE

(76) Inventors: Chamkurkishtiah P. Rao, Mohawk, NY (US); Diana C. Lister, New Hartford, NY (US)

( * ) Notice: Subject to any disclaimer, the term of this patent is extended or adjusted under 35 U.S.C. 154(b) by 1336 days.

(21) Appl. No.: 11/785,592

(22) Filed: Apr. 18, 2007

(65) Prior Publication Data

US 2008/0257355 A1    Oct. 23, 2008

(51) Int. Cl.
*A61M 11/00* (2006.01)
(52) U.S. Cl. .......... 128/207.14; 128/207.15; 128/200.26
(58) Field of Classification Search ............ 128/200.26, 128/207.14, 207.15, 207.16, 909, 200.24; 250/455.1
See application file for complete search history.

(56) References Cited

U.S. PATENT DOCUMENTS

| | | | |
|---|---|---|---|
| 3,948,273 A * | 4/1976 | Sanders .................. 128/207.15 |
| 4,021,265 A | 5/1977 | Guenther | |
| 5,061,255 A | 10/1991 | Greenfeld et al. | |
| 5,687,714 A | 11/1997 | Kolobow et al. | |
| 5,715,815 A | 2/1998 | Lorenzen et al. | |
| 5,775,325 A * | 7/1998 | Russo .................. 128/205.12 |
| 5,819,723 A | 10/1998 | Joseph | |
| 5,855,203 A * | 1/1999 | Matter .................. 128/207.14 |
| 6,082,361 A | 7/2000 | Morejon | |
| 6,258,195 B1 | 7/2001 | Holman et al. | |
| 6,330,883 B1 * | 12/2001 | Berger .................. 128/201.13 |
| 6,494,208 B1 | 12/2002 | Morejon | |
| 6,551,346 B2 | 4/2003 | Crossley | |
| 6,736,841 B2 | 5/2004 | Musbach et al. | |
| 6,890,348 B2 | 5/2005 | Sydney et al. | |
| 6,942,648 B2 | 9/2005 | Schaible et al. | |
| 7,051,737 B2 | 5/2006 | Kolobow et al. | |
| 7,159,590 B2 * | 1/2007 | Rife .................. 128/207.15 |
| 7,179,849 B2 * | 2/2007 | Terry .................. 523/122 |
| 2002/0018866 A1 | 2/2002 | Lee et al. | |
| 2005/0251119 A1 | 11/2005 | Eaton et al. | |

FOREIGN PATENT DOCUMENTS

DE    102005023018    11/2006

OTHER PUBLICATIONS

"Machining self-cleaning surfaces using laser ablation", *SenterNovem*, Oct. 2004, 4 pages, printed on Apr. 11, 2007 from http://www.senternovem.nl/mmfiles/Factsh%20Lotus_UK_tcm24-194387.pdf.
"Inhibition of adhesion of yeasts and bacteria by poly(ethylene oxide)-brushes on glass in a parallel plate flow chamber", *Microbiology*, 149, 3239-3246 (2003).
"Synthesis of Titanium Dioxide ($TiO_2$) Nanomaterials", *Journal of Nanoscience and Nanotechnology*, vol. 6, 906-925 (2006).

(Continued)

*Primary Examiner* — Steven Douglas
(74) *Attorney, Agent, or Firm* — Richard C. Litman

(57) ABSTRACT

The self-cleaning and sterilizing endotracheal and tracheostomy tube may include a combination of an endotracheal tube or a tracheostomy tube and a suction catheter that decreases the tendency of mucus and bacteria to adhere to the inner surfaces of the thereof. The endotracheal tube and the catheter may have a hydrophobic surface exhibiting the lotus effect, which may be formed either by femtosecond laser etching or by a coating of ploy (ethylene oxide). Alternatively, the endotracheal tube and the catheter may have a lumen coated with a photocatalyst. The endotracheal tube may also have a light source and a fiberoptic bundle mounted thereon, the optical fibers extending into the lumen to illuminate the photocatalyst.

19 Claims, 6 Drawing Sheets

OTHER PUBLICATIONS

"New nanocomposite polymer for medical devices", printed from http://www.azonano.com/news.asp?newsID=2533, 3 pages; printed on Apr. 16, 2007.

"Nanotechnology Delivers Microcoatings"; printed from http://www.devicelink.com/mdt/archive/06/10/002.html; 2 pages; printed on Apr. 16, 2007.

B. Li and B.E. Logan, "The impact of ultraviolet light on bacterial adhesion to glass and metal oxide-coated surface", *Colloids Surf B Biointerfaces*, Mar. 25, 2005, 41(2-3): 153-161, Epub (2005).

B. Neppolian et al., "Solar/UV-induced photocatalytic degradation of three commercial textile dyes", J. Hazrd Mater., Jan. 28, 2002; 89(2-3): 303-317.

K. Nagaveni et al., "Photocatalytic degradation of organic compounds over combustion-synthesized nano-TiO2", *Environ. Sci. Technol.*, Mar. 1, 2004, 38(5):1600-1604.

D. Zhang et al., "Room-temperature preparation of nanocrystalline TiO2 films and the influence of surface properties on dye-sensitized solar energy conversion", *J. Phys. Chem. B Condens. Matter Mater. Surf. Interfaces Biophys.*, Nov. 2, 2006, 110(43):21890-21898.

* cited by examiner

SELF-CLEANING AND STERILIZING ENDOTRACHEAL AND TRACHEOSTOMY TUBE

BACKGROUND OF THE INVENTION

1. Field of the Invention

The present invention relates to endotracheal or tracheostomy tubes and suction catheters used with such tubes, and particularly to a self-cleaning and sterilizing endotracheal or tracheostomy tube, and an associated suction catheter for use with the endotracheal or tracheostomy tube.

2. Description of the Related Art

In human beings, mucociliary action regulates the flow of mucus across the layers of epithelial cells within air passages. When a person experiences breathing difficulty or occlusion, an endotracheal tube is often inserted within the person's air passage. The endotracheal tube, however, interferes with the cilia of the epithelial cells, thus disrupting the mucociliary action. This often causes the accumulation of mucus about or within the endotracheal tube. This accumulation of mucus not only occludes the endotracheal tube passage, but can result in the accumulation and adhesion of bacteria and other microbes to the endotracheal tube, with resulting pulmonary infections.

Suction catheters are typically provided, either separately or in combination with the endotracheal tube, for removal of the accumulated mucus. Although the function of the suction catheter is to remove the mucus, excess mucus may adhere to the surface of the suction catheter, which results in impaired functioning thereof and may result in unwanted mucus remaining on the endotracheal tube. This may result in contamination of both the suction catheter and the endotracheal tube and in the inefficient operation of one or both. Furthermore, while a suction catheter is effective in removing watery mucous, the suction catheter is ineffective at removing mucous that has collected and dried on the wall of the endotracheal tubing, or on the catheter itself.

Thus, a self-cleaning and sterilizing endotracheal tube solving the aforementioned problems is desired.

SUMMARY OF THE INVENTION

The self-cleaning and sterilizing endotracheal tube provides a combination endotracheal tube and suction catheter, which decreases the tendency of mucus and bacteria to adhere to the inner surfaces of the endotracheal tube and the suction catheter. The endotracheal tube defines a lumen for maintaining a patient's airway. The endotracheal tube is made from a flexible nano-composite polymer, such as polyvinyl chloride or silicone rubber, the lower portion of the tube being adapted for passage into the patient's trachea.

The suction catheter is a flexible tube made from the same material as the endotracheal tube, and can be passed through the lumen of the endotracheal tube while still leaving room for the passage of air through the endotracheal tube in an annular passage around the catheter. A fitting may be attached to the upper end of the catheter equipped with various ports so that the catheter may alternatively be connected to a vacuum source to provide suction, an irrigation port for lavage, for passage of an endoscope, etc.

The inner surfaces of the suction catheter and the endotracheal tube may be made self-cleaning and sterilizing several different ways. The inner surfaces may be provided with a "lotus effect" either by laser etching the tubing and catheter, or a mold used to form the tubing and catheter, with a femtosecond laser, or by coating the tubing with a hydrophobic material that produces the same effect. The lotus effect refers to the structure of the lotus leaf, which is covered with tiny pillars. Water drops are carried up the pillars, form a spherical shape, and fall down the pillars, carrying away any accumulated dirt. The same surface effect can be achieved with laser etching, or by applying certain hydrophobic coatings, such as poly (ethylene oxide).

Alternatively, the inner surfaces of the endotracheal tube and the catheter may be coated with a photocatalytic material with antimicrobial properties when exposed to ultraviolet light. Such materials may include titanium oxide, silicon oxide, zinc oxide, zirconium oxide, cadmium sulfate, metal oxides or combinations thereof. A light source, such as a light emitting diode (LED), which may be a UV LED, is attached to an upper portion of the endotracheal tube. Light emitted by the light source is carried by a fiberoptic bundle. The fibers pass through the endotracheal tube and illuminate the photocatalytic material in one of two ways.

In a first embodiment, an uncoated portion of the fibers extends axially within the lumen of the endotracheal tube, emitting light radially. In this embodiment, the lumen is lined with a UV reflective barrier and the photocatalytic material is transparent. In a second embodiment, the fibers are coated, but terminate at different lengths, providing point sources that are directed radially inward into the lumen of the endotracheal tube. The photocatalytic material need not be transparent in this embodiment. In either embodiment, the lumen of the suction catheter is also coated with a photocatalytic material. The suction catheter is positioned outside the endotracheal tube when not in use, and may be exposed to UV or solar visible light externally and/or intraluminally.

Self-cleaning results from decreased adherence of biomatter to the walls of the endotracheal tube and suction catheter upon exposure to UV light, by the photocatalytic production of substances toxic to bacteria and other microbes, and/or by exposure to UV radiation at wavelengths known to exhibit antimicrobial activity (185 nm, 254 nm, and 265 nm).

The endotracheal tube and suction catheter may also be made self-cleaning and sterilizing by a combination of the hydrophobic surface and the fiberoptic-photocatalytic coatings, if desired. The scope of the present invention also extends to a tracheostomy tube, which has the same appearance and structure as the endotracheal tube, but is shorter in length, being designed for insertion into a tracheostomy stoma below the larynx.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is directed towards a self-cleaning and sterilizing endotracheal tube, which may include a combination endotracheal tube and suction catheter 10 that decreases the tendency of mucus and bacteria to adhere to the inner surfaces of the endotracheal tube and the suction catheter.

Figure 1:
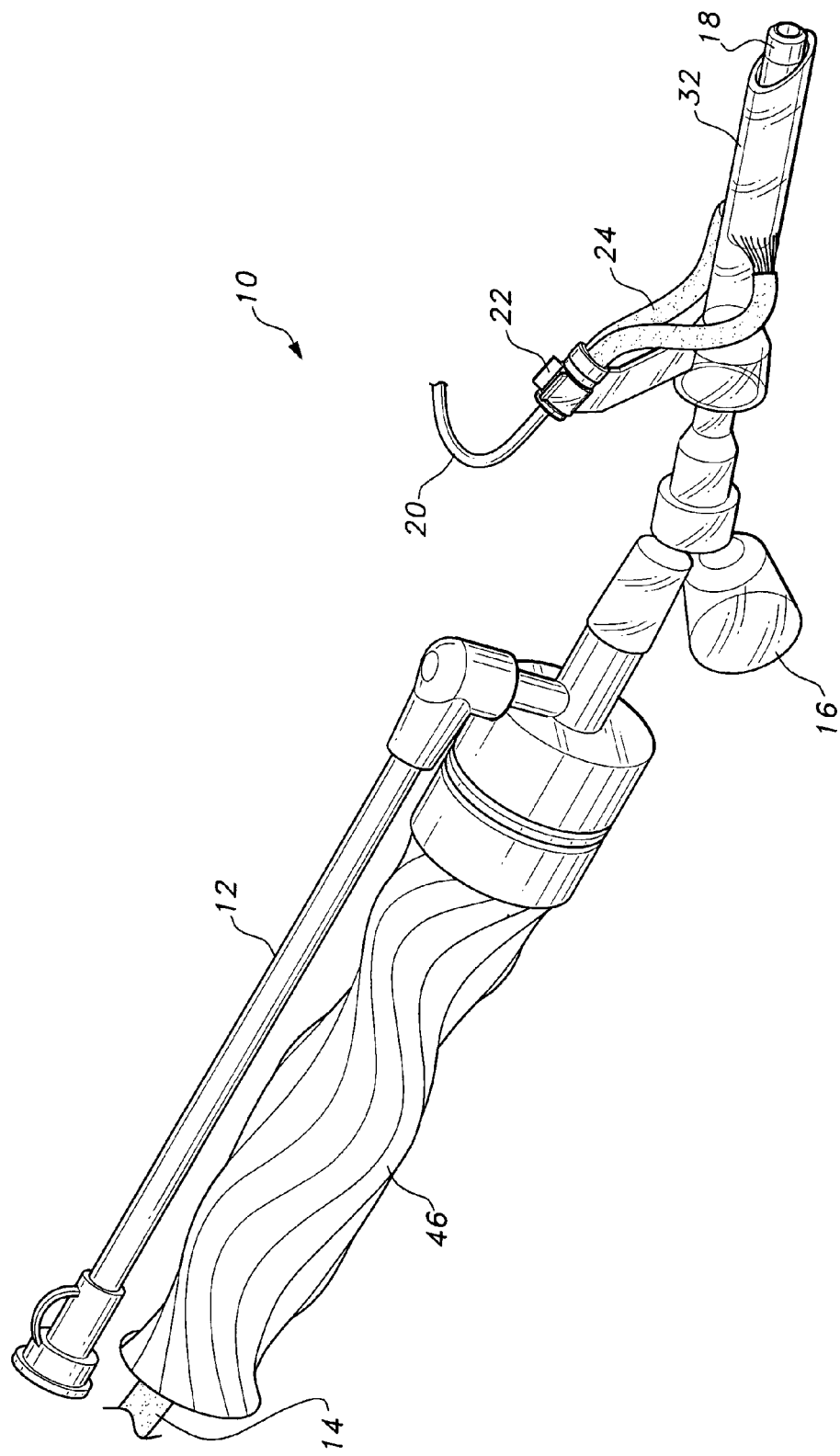
FIG. 1 is an environmental perspective view of a self-cleaning and sterilizing endotracheal tube according to the present invention.
Figure 2:
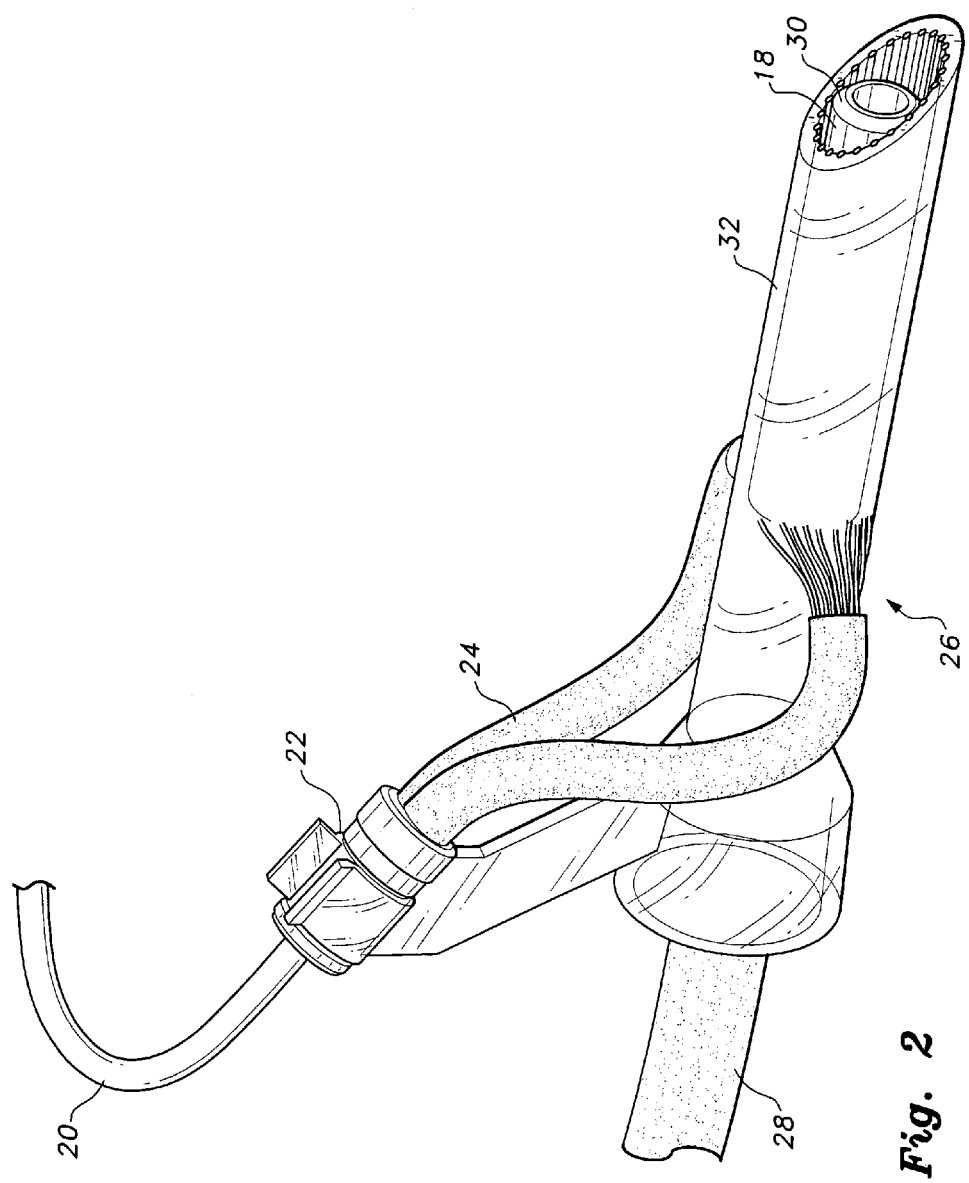
FIG. 2 is an environmental perspective view of the self-cleaning and sterilizing endotracheal tube according to the present invention with a suction catheter inserted therein.

As best shown in FIG. 2, the combination 10 includes an endotracheal tube 32 and a suction catheter 18. As shown in FIG. 1, a fitting may be attached to the suction catheter with ports for connection of a vacuum tube 14 (which may have a fluted gripping surface 46) for the application of suction, an irrigation tube 12 for lavage, and an endotracheal tube adapter for insertion of an endoscope or other device through the catheter. The endotracheal tube 32 has a lower portion adapted for insertion into a patient's trachea and defines a lumen for maintaining patentcy of the patient's airways. The diameter of the endotracheal tube lumen is large enough to permit passage of the suction catheter 14 therethrough and maintain the passage of air through an annular passage between the catheter 14 and the endotracheal tube 32.

In the preferred embodiment, suction catheter 14 and lower portion 32 are formed from flexible nano-composite polymers, which will be comfortable for the patient, and which will not degrade or corrode in the presence of bodily fluids. Such materials may include polyvinyl chloride or silicone rubber. Further, as best shown in FIG. 1, the lower end of the endotracheal tube 32 is beveled, allowing for easy and comfortable insertion within the patient's trachea, the lower end 30 of the suction catheter 18 extending through the lower end of endotracheal tube 32. It should be understood that the endotracheal tube may be shaped, sized or formed from materials adapted for use in maintaining the patient's airways, and that the scope of the present invention also extends to a tracheostomy tube, which has the same structure as the endotracheal tube 32, but is shorter in length, being adapted for insertion through a tracheosotmy stoma below the larynx.

The endotracheal tube 32 may be made self-cleaning and sterilizing by providing the inner surface 44 of the tube 32 defining the lumen with a hydrophobic surface. Similarly, the suction catheter 18 may be made self-cleaning and sterilizing by providing the inner surface 34 defining the lumen of the suction catheter 18 with a hydrophobic surface in order to reduce the tendency of mucus and bacteria to adhere thereto.

Such a hydrophobic surface may be formed to exhibit the "lotus effect." The lotus effect refers to the structure of the lotus leaf, which is covered with tiny pillars. Water drops are carried up the pillars, form a spherical shape, and fall down the pillars, carrying away any accumulated dirt. Such a surface is shown in the microscopic view of FIG. 5B, with alternating rows of peaks 60 and valleys 62 defining the pillars. The hydrophobic surface may be formed by laser etching the interior surfaces 44 and 34 of the tube 32 and the catheter 18, respectively, with a femtosecond laser forming perpendicular lines, or by shaping a mold for extrusion or injection molding of the tube 32 and catheter 18 with femtosecond laser pulses. Alternatively, the hydrophobic surface may be formed by coating the inner surfaces 44 and 34 with a hydrophobic material, such as poly (ethylene oxide), which forms chains of polymer defining the pillars in the lumens of the endotracheal tube 32 and suction catheter 18.

Alternatively, the inner surfaces may be coated with a photocatalytic material with antimicrobial properties when exposed to ultraviolet light, or other selective ranges of electromagnetic radiation. Such antibacterial coating materials may include, for example, titanium oxide, silicon oxide, zinc oxide, zirconium oxide, cadmium sulfate, other metal oxides or combinations thereof. It is well known that doping the above materials with nitrogen or sulfur allows for photocatalysis thereof in the presence of solar or visible light. It should be understood that the photocatalytic surface may be combined with the hydrophobic surface of FIG. 5B.

In order to provide for photocatalysis within the endotracheal tube 32, an illumination source 22 is mounted to the exterior of the endotracheal tube 32 by a bracket attached to the tube 32 by an arm extending from an upper portion of the tube 32. The illumination source 22 may comprise an LED. The illumination source 22 may comprise a source of ultraviolet light, such as one or more ultraviolet light emitting diodes. The illumination source may further comprise a light source capable of emitting ultraviolet light at wavelengths known to exhibit antimicrobial activity, such as 185 nm, 254 nm and 265 nm, or at wavelengths known to induce optimal photocatalytic activity in the particular coating used, such as 254 nm for titanium dioxide. A power cord 20 is provided for connection with a suitable source of electrical current.

A fiberoptic bundle is further provided, with each optical fiber having an upper end and a lower end. The upper ends 26 thereof are in direct optical communication with the illumination source 22, and are shown in FIG. 2 as being bundled together within fiberoptic cable harnesses 24. The fibers pass through the endotracheal tube 32 and provide illumination to the photocatalytic coating in one of two ways.

Figure 3:
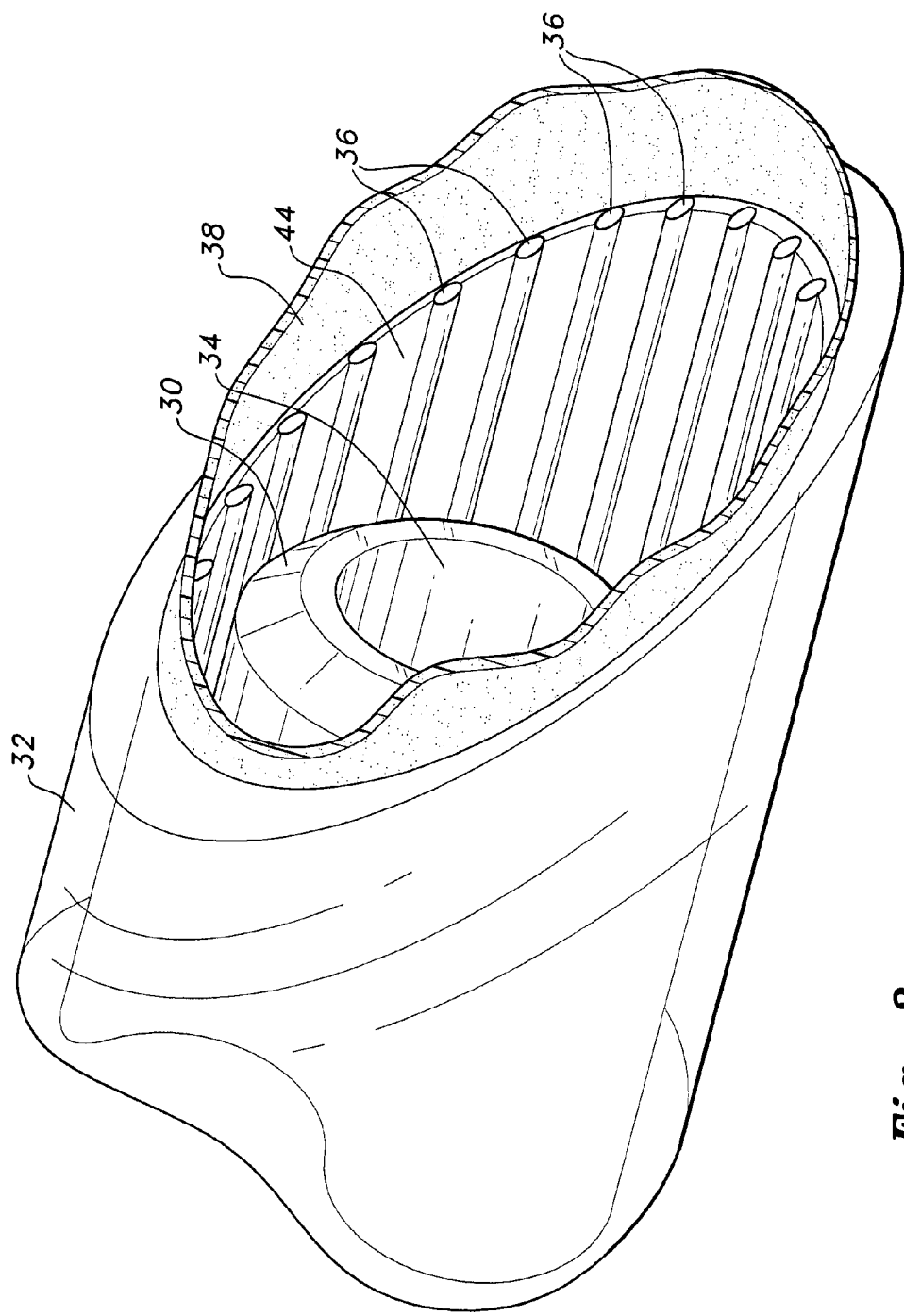
FIG. 3 is a partial perspective view of the self-cleaning and sterilizing endotracheal tube according to the present invention, broken away and partially in section to show details of the invention.

In the embodiment shown in FIG. 3, the lower ends 36 of the optical fibers are uncoated, and extend axially along the inner wall 44 of the endotracheal tube 32. In this embodiment, the light projects along a substantially radial direction through the walls of the optical fibers. In this embodiment, the photocatalytic coating is transparent, and a UV reflector 38 is disposed between the fibers 36 and the exterior of the tube 32.

Figure 4:
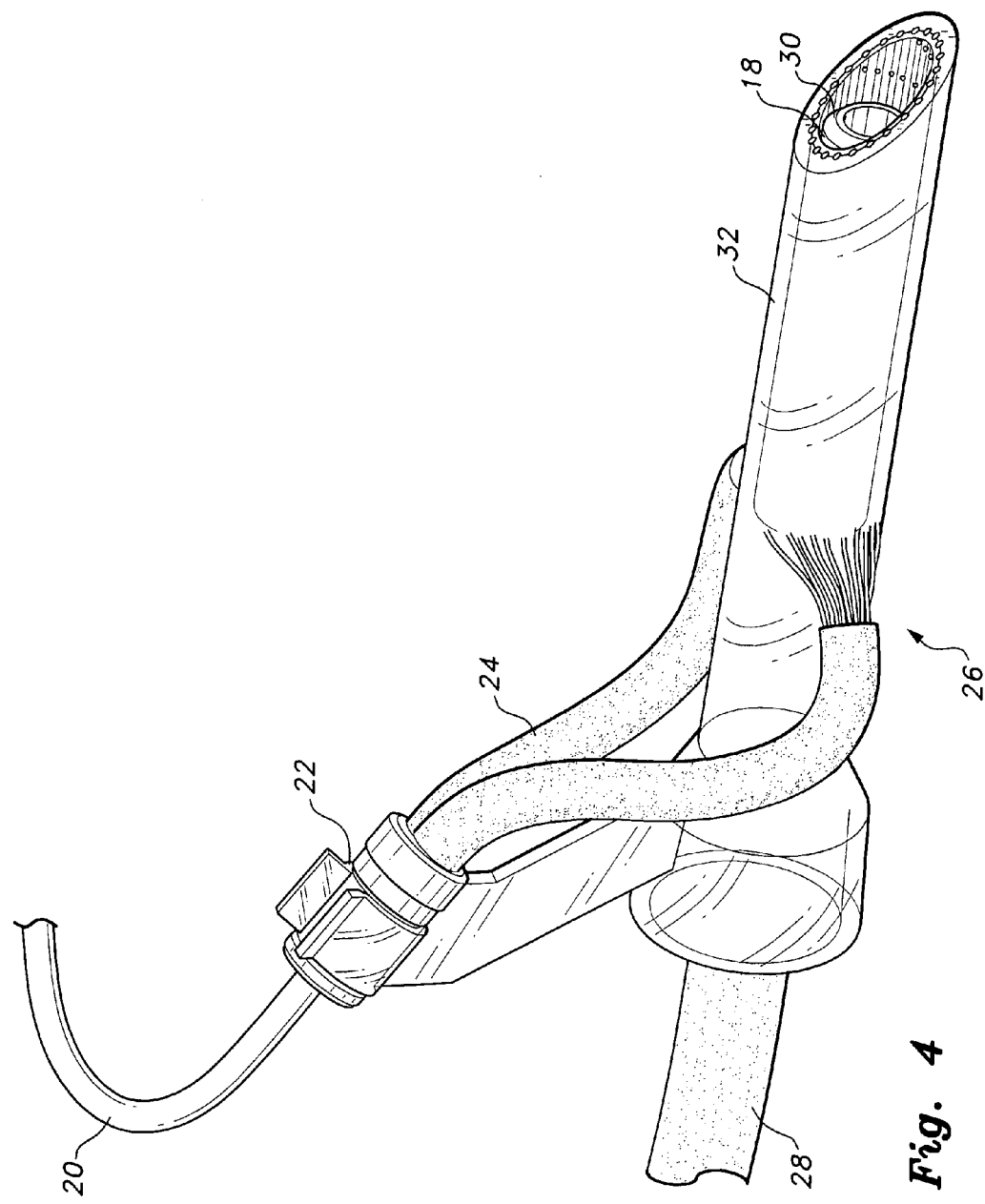
FIG. 4 is an environmental perspective view of an alternative embodiment of the self-cleaning and sterilizing endotracheal tube according to the present invention.
Figure 5A:
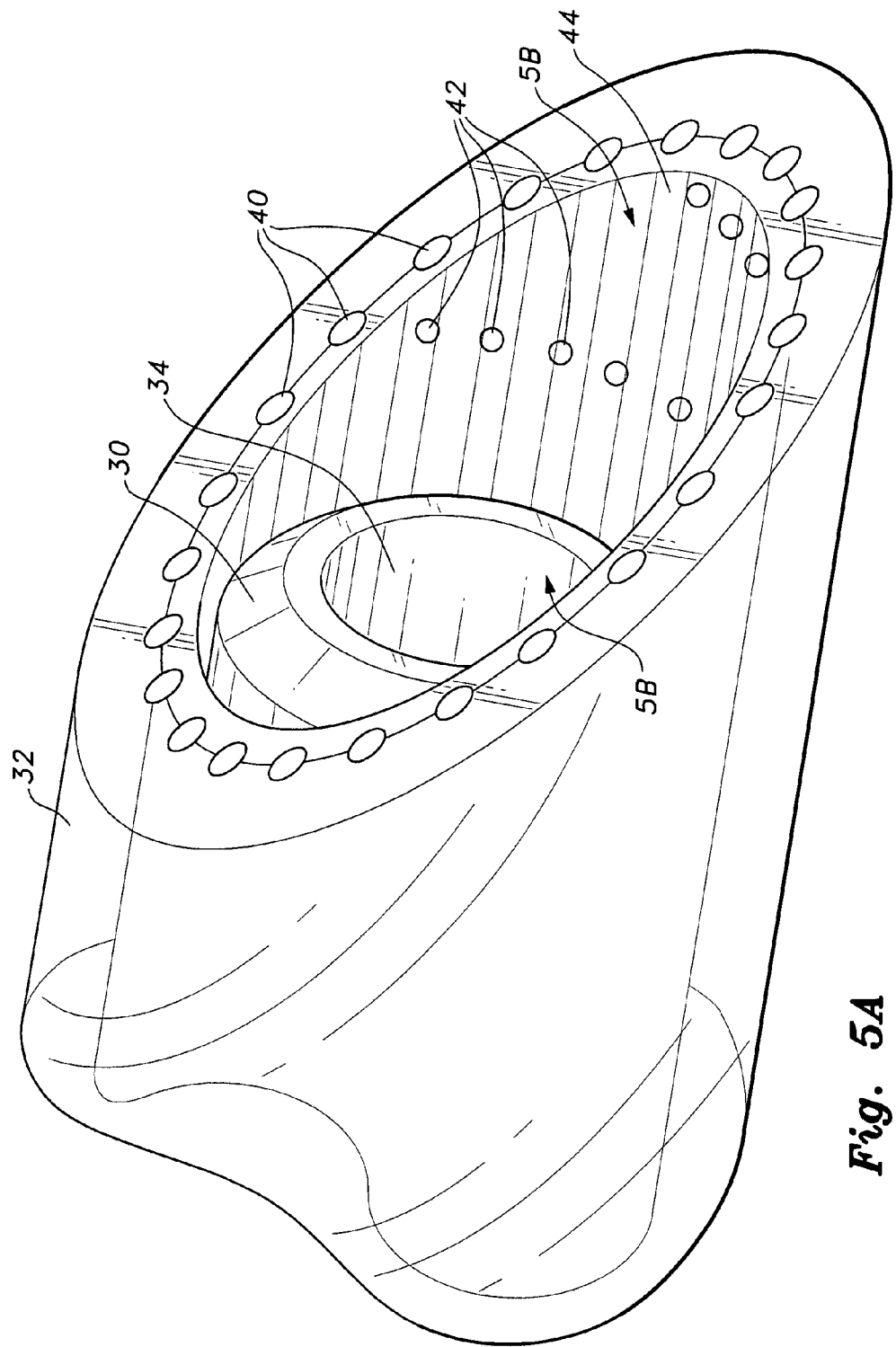
FIG. 5A is a partial perspective view of the endotracheal tube of FIG. 4, broken away and partially in section to show details thereof.
Figure 5B:
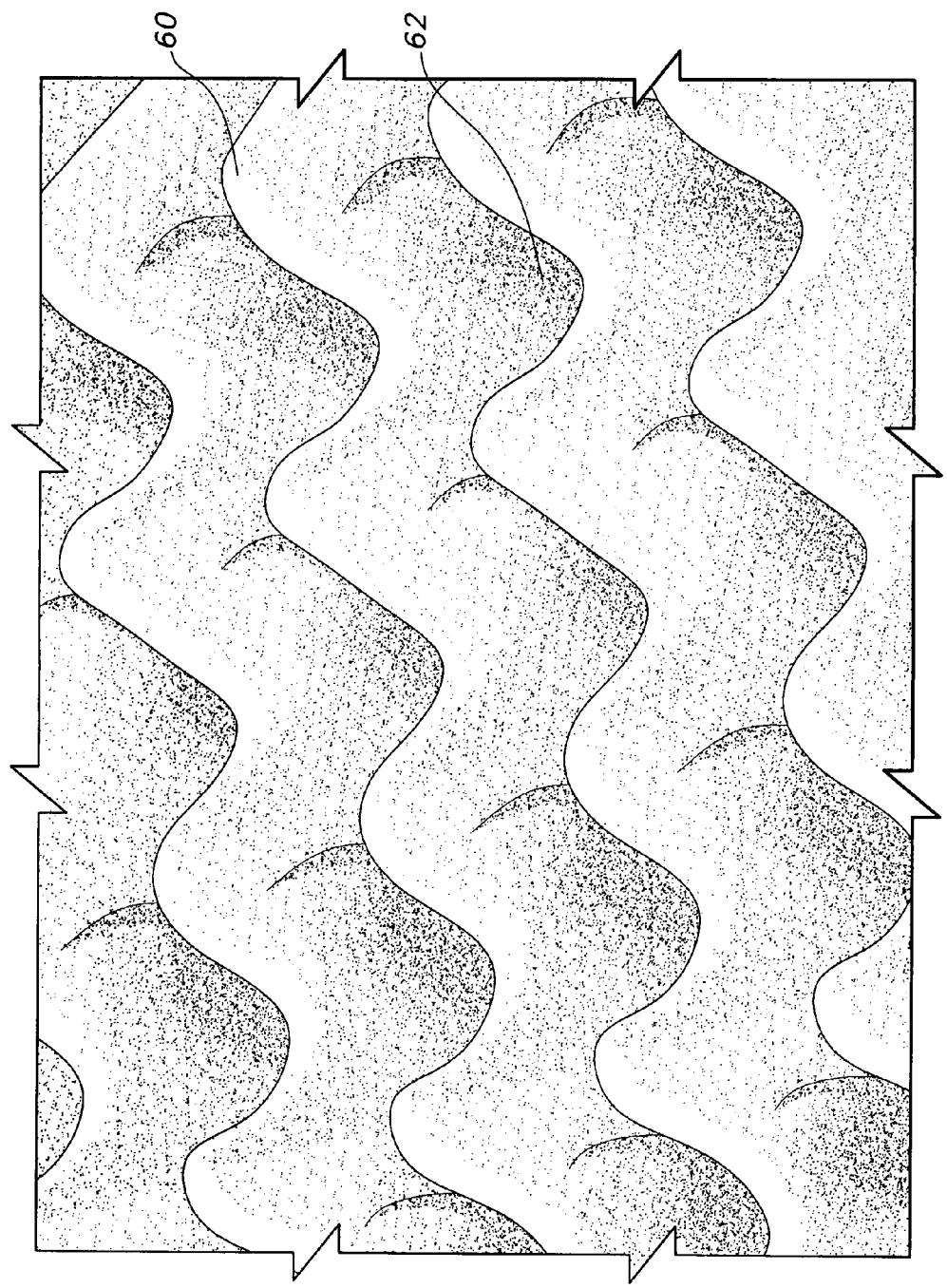
FIG. 5B shows a partial, microscopic view of a hydrophobic surface formed on the inner surfaces of the endotracheal tube and suction catheter according to an embodiment of the present invention.

Alternatively, as shown in FIGS. 4 and 5A, optical fibers may have different lengths with the lower ends 42 of the optical fibers 40 being directed radially to form point sources of light directed into the lumen of the tube 32. In this embodiment, the fibers are coated throughout their length, and may be attached to or embedded within the wall of the tube 32. In this embodiment, there is no UV reflector disposed in the wall of the tube 32, and the photocatalytic coating need not be transparent.

The tube 32 is rendered self-cleaning and sterilizing by illuminating the photocatalyst, either through decreasing adherence of biomatter to the walls of the tube 32 by UV radiation, by production of substances toxic to bacteria through photocatalytic activity, and/or by irradiation with UV light at wavelengths known to exhibit antimicrobial activity.

When not in use, the suction catheter 18 is preferably removed from the endotracheal tube 38. The suction catheter 14 may be sterilized through irradiation with ultraviolet light externally and/or intraluminally, or by solar or visible light when the photocatalyst has been doped with nitrogen or sulfur. Further, although shown as being applied to an endotracheal tube, it should be understood that the above arrangement may further be used with a tracheostomy tube or the like.

It will be understood that the tube 32 may be rendered self-cleaning and sterilizing through a combination of a hydrophobic surface exhibiting the lotus effect and through a fiberoptic endotracheal tube illuminating a photocatalyst, if desired. Further, it should be understood that the endotracheal tube shown in the Figures is for exemplary purposes only, and that the present invention may be applied to any suitable endotracheal tube or tracheostomy tube, dependent upon the needs and desires of the user.

It is to be understood that the present invention is not limited to the embodiments described above, but encompasses any and all embodiments within the scope of the following claims.

We claim:

1. A self-cleaning and sterilizing endotracheal tube, comprising:
   an elongate tube formed of flexible nano-composite polymer material having an upper portion and a lower portion, the tube defining a lumen, the lower portion being adapted for insertion into a patient's trachea in order to maintain patentcy of the patient's airway; and
   means for rendering the tube self-cleaning and sterilizing in order to prevent narrowing of the lumen and buildup of mucous and bacteria in the lumen, wherein the means for rendering the tube self-cleaning and sterilizing includes a hydrophobic surface formed by femtosecond laser etched perpendicular lines formed in the surface and exhibiting a lotus effect formed in the lumen of the tube.

2. The self-cleaning and sterilizing endotracheal tube according to claim 1, wherein said hydrophobic surface comprises a coating formed from chains of poly (ethylene oxide) disposed in the lumen of said tube.

3. A self-cleaning and sterilizing endotracheal tube, comprising:
   an elongate tube formed of flexible nano-composite polymer material having an upper portion and a lower portion, the tube defining a lumen, the lower portion being adapted for insertion into a patient's trachea in order to maintain patentcy of the patient's airway; and
   means for rendering the tube self-cleaning and sterilizing in order to prevent narrowing of the lumen and buildup of mucous and bacteria in the lumen, wherein the means for rendering the tube self-cleaning and sterilizing comprises:
   i) a light source mounted on said tube;
   ii) a fiberoptic bundle having fibers extending into the lumen; and
   iii) a photocatalyst coated on the inner surface defining the lumen of the tube.

4. The self-cleaning and sterilizing endotracheal tube according to claim 3, wherein said light source comprises a source of ultraviolet light.

5. The self-cleaning and sterilizing endotracheal tube according to claim 4, wherein said source of ultraviolet light emits UV radiation at an antimicrobial wavelength selected from the group consisting of 185 nm, 254 nm, and 265 nm.

6. The self-cleaning and sterilizing endotracheal tube according to claim 4, wherein said light source comprises an LED.

7. The self-cleaning and sterilizing endotracheal tube according to claim 4, wherein said light source comprises an ultraviolet LED.

8. The self-cleaning and sterilizing endotracheal tube according to claim 4, wherein the fibers extending into the lumen of the tube include an uncoated portion extending axially within the lumen of the tube, the uncoated portion emitting light radially into the lumen.

9. The self-cleaning and sterilizing endotracheal tube according to claim 8, further comprising a UV reflector disposed between the uncoated portion of the fibers and an exterior surface of the tube.

10. The self-cleaning and sterilizing endotracheal tube according to claim 8, wherein said photocatalytic coating is transparent.

11. The self-cleaning and sterilizing endotracheal tube according to claim 4, wherein the fibers extending into the lumen of the tube are coated and have different lengths, the fibers having ends directed radially into the lumen of the tube, defining point sources of light.

12. The self-cleaning and sterilizing endotracheal tube according to claim 4, wherein said photocatalyst is selected from the group consisting of titanium oxide, silicon oxide, zinc oxide, zirconium oxide, and cadmium sulfate.

13. The self-cleaning and sterilizing endotracheal tube according to claim 4, further comprising an arm extending from said tube, said light source being mounted on said arm.

14. The self-cleaning and sterilizing endotracheal tube according to claim 13, wherein said photocatalyst is selected from the group consisting of titanium oxide, silicon oxide, zinc oxide, zirconium oxide, and cadmium sulfate, said photocatalyst being doped with nitrogen or sulfur.

15. The self-cleaning and sterilizing endotracheal tube according to claim 1, further comprising a suction catheter removably inserted into said tube, the suction catheter defining a lumen.

16. The self-cleaning and sterilizing endotracheal tube according to claim 15, wherein the lumen of said catheter has a hydrophobic surface exhibiting a lotus effect, said hydrophobic surface being formed by femtosecond laser etched perpendicular lines formed in the surface.

17. The self-cleaning and sterilizing endotracheal tube according to claim 15, wherein the lumen of said catheter has a hydrophobic surface exhibiting a lotus effect, said hydrophobic surface comprising a coating formed from chains of poly (ethylene oxide) disposed in the lumen of said tube.

18. A self-cleaning and sterilizing endotracheal tube, comprising:
   an elongate tube formed of flexible nano-composite polymer material, the elongate tube including a photocatalytic material having antimicrobial properties and having an upper portion and a lower portion, the tube defining a lumen, the lower portion being adapted for insertion into a patient's trachea in order to maintain patentcy of the patient's airway;
   a light source mounted on the tube;
   a fiberoptic bundle having fibers extending into the lumen, whereby the tube is self-cleaning and sterilizing when exposed to the light source thereby inhibiting the narrowing of the lumen and buildup of mucous and bacteria in the lumen.

19. The self-cleaning and sterilizing endotracheal tube according to claim 18, wherein said light source comprises a source of ultraviolet light.

* * * * *